(12) United States Patent
Hashimshony et al.

(10) Patent No.: US 8,449,477 B2
(45) Date of Patent: May 28, 2013

(54) DEVICE AND METHOD FOR TRANSPORTING AND HANDLING TISSUE

(75) Inventors: Dan Hashimshony, Givat Ada (IL); Orit Yarden, Givat Shmuel (IL); Gal Aharonowitz, Moshav Gan Haim (IL); Gil Cohen, Jerusalem (IL); Iddo Geltner, Herzlia (IL)

(73) Assignee: Dune Medical Devices Ltd., Caesaria (IL)

( * ) Notice: Subject to any disclaimer, the term of this patent is extended or adjusted under 35 U.S.C. 154(b) by 0 days.

(21) Appl. No.: 10/582,135

(22) PCT Filed: Mar. 2, 2006

(86) PCT No.: PCT/IL2006/000288
§ 371 (c)(1),
(2), (4) Date: Jun. 8, 2006

(87) PCT Pub. No.: WO2006/092797
PCT Pub. Date: Sep. 8, 2006

(65) Prior Publication Data
US 2008/0249434 A1 Oct. 9, 2008

Related U.S. Application Data

(60) Provisional application No. 60/657,410, filed on Mar. 2, 2005.

(51) Int. Cl.
*A61B 10/00* (2006.01)

(52) U.S. Cl.
USPC .......................... 600/562; 206/527; 378/163

(58) Field of Classification Search
USPC .......................... 600/562; 221/210; 378/163
See application file for complete search history.

(56) References Cited

U.S. PATENT DOCUMENTS

| 3,743,084 A | * | 7/1973 | Douglas | 206/532 |
|---|---|---|---|---|
| 4,923,458 A | * | 5/1990 | Fischer | 606/59 |
| 5,105,457 A | * | 4/1992 | Glassman | 378/163 |
| 5,325,767 A | * | 7/1994 | Beller | 99/421 R |
| 5,383,234 A | * | 1/1995 | Russell | 378/164 |

(Continued)

FOREIGN PATENT DOCUMENTS

| WO | WO 02/059571 | * 10/2001 |
|---|---|---|
| WO | WO 2006/092797 | 9/2006 |

OTHER PUBLICATIONS

International Preliminary Report on Patentability Dated Sep. 20, 2007 From the International Bureau of WIPO Re.: Application No. PCT/IL2006/000288.

(Continued)

*Primary Examiner* — Max Hindenburg
*Assistant Examiner* — Renee Danega

(57) ABSTRACT

A device and method are provided for tissue handling, while maintaining the in-vivo tissue orientation. The device includes a structure, configured for receiving and holding a tissue specimen, wherein the tissue specimen includes tissue positional references; and device positional references, associated with the structure, for fixing the orientation of the tissue specimen, when held by the device, so as to reflect the tissue specimen positional references.

36 Claims, 14 Drawing Sheets

U.S. PATENT DOCUMENTS

| | | | | |
|---|---|---|---|---|
| 5,524,633 | A | * | 6/1996 | Heaven et al. ............... 600/562 |
| 5,568,534 | A | * | 10/1996 | Watkins ..................... 378/208 |
| 5,609,827 | A | | 3/1997 | Russell et al. |
| 5,766,173 | A | * | 6/1998 | Ross et al. ..................... 606/56 |
| 5,913,857 | A | | 6/1999 | Ritchart et al. |
| 5,961,515 | A | * | 10/1999 | Taylor et al. ................. 606/59 |
| 6,007,497 | A | | 12/1999 | Huitema |
| 6,035,808 | A | * | 3/2000 | Herman ..................... 119/732 |
| 6,225,107 | B1 | * | 5/2001 | Nagle ....................... 435/283.1 |
| 7,645,279 | B1 | * | 1/2010 | Haupt ........................... 606/54 |

OTHER PUBLICATIONS

International Search Report and the Written Opinion Dated Nov. 2, 2006 From the International Searching Authority Re.: Application No. PCT/IL06/00288.

Official Action Dated May 5, 2009 From the US Patent and Trademark Office Re.: U.S. Appl. No. 10/582,135.

Official Action Dated Aug. 14, 2008 From the US Patent and Trademark Office Re.: U.S. Appl. No. 10/582,135.

* cited by examiner

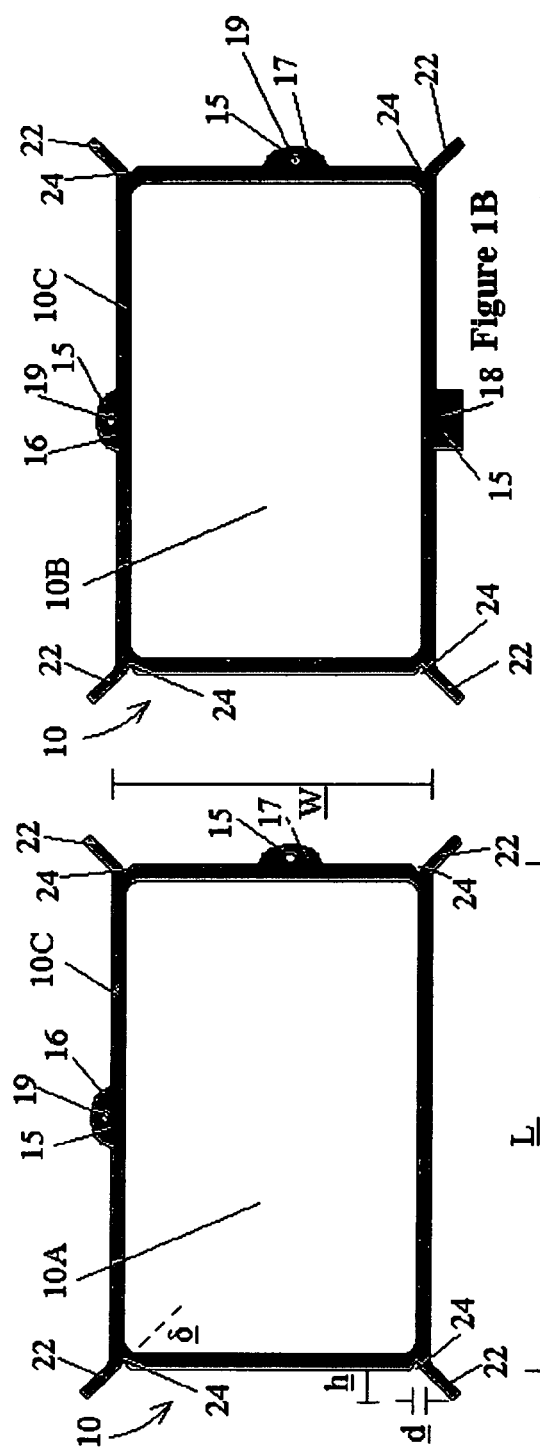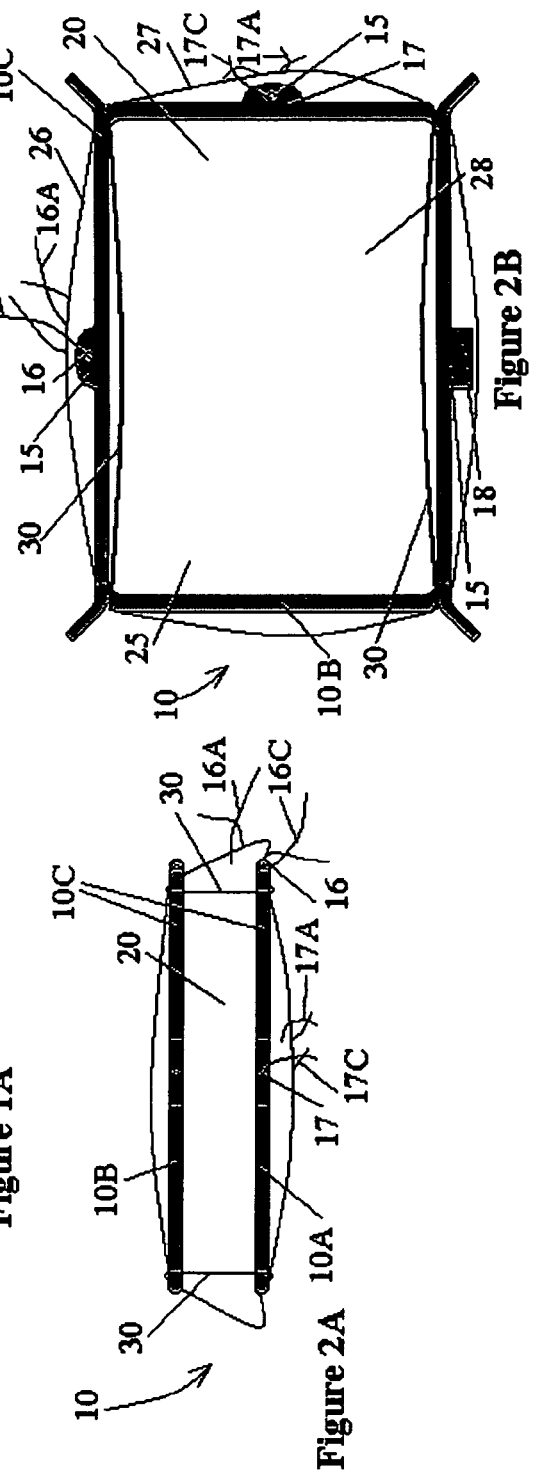

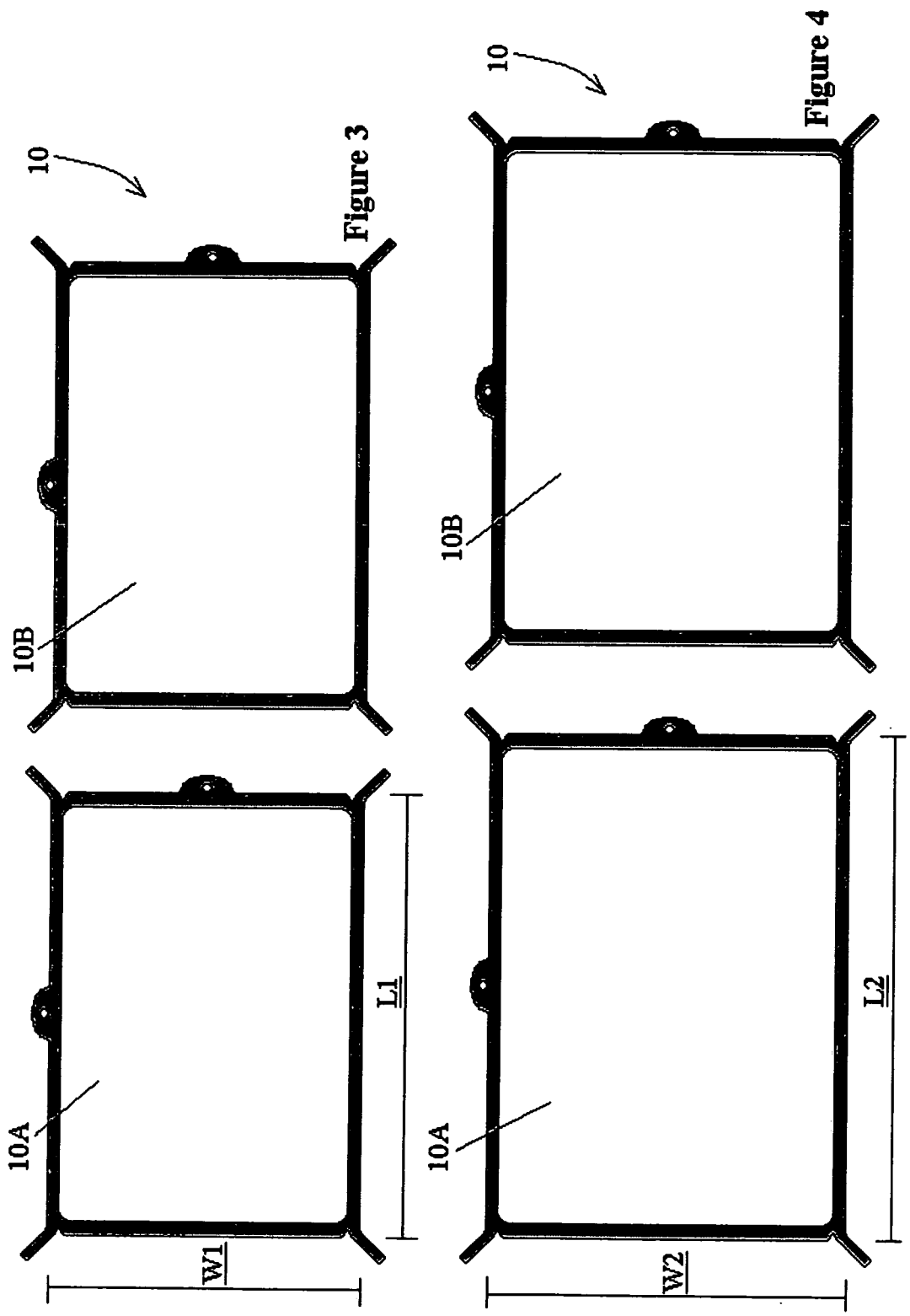

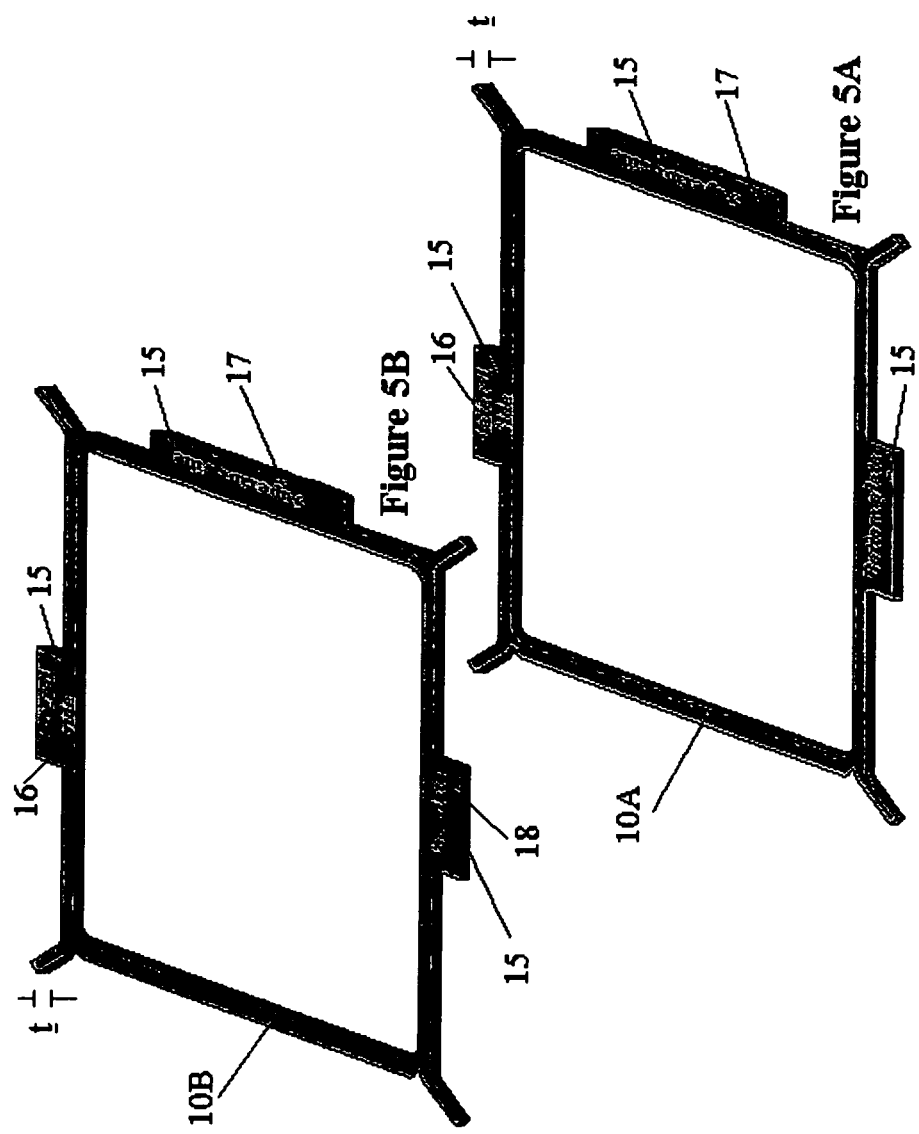

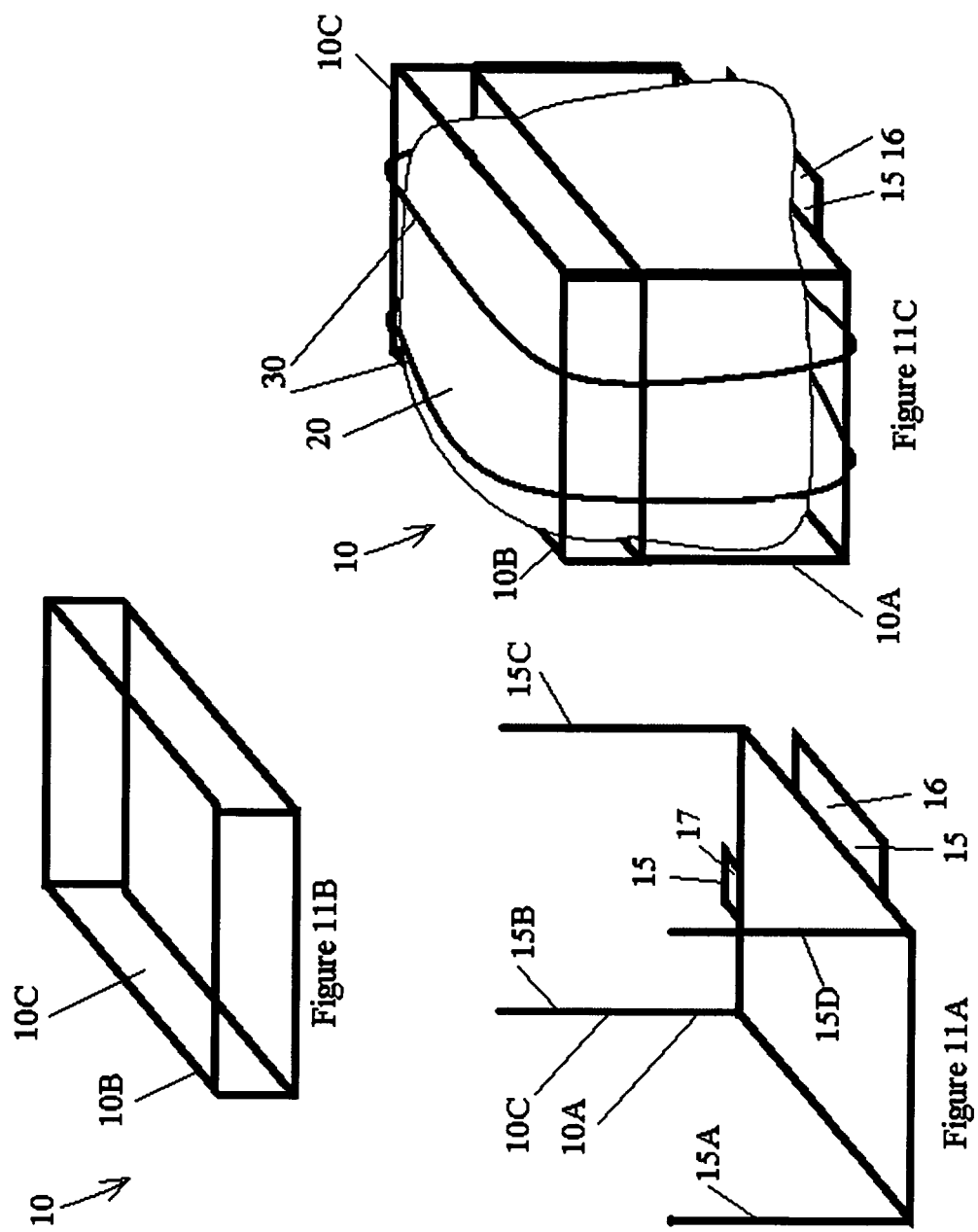

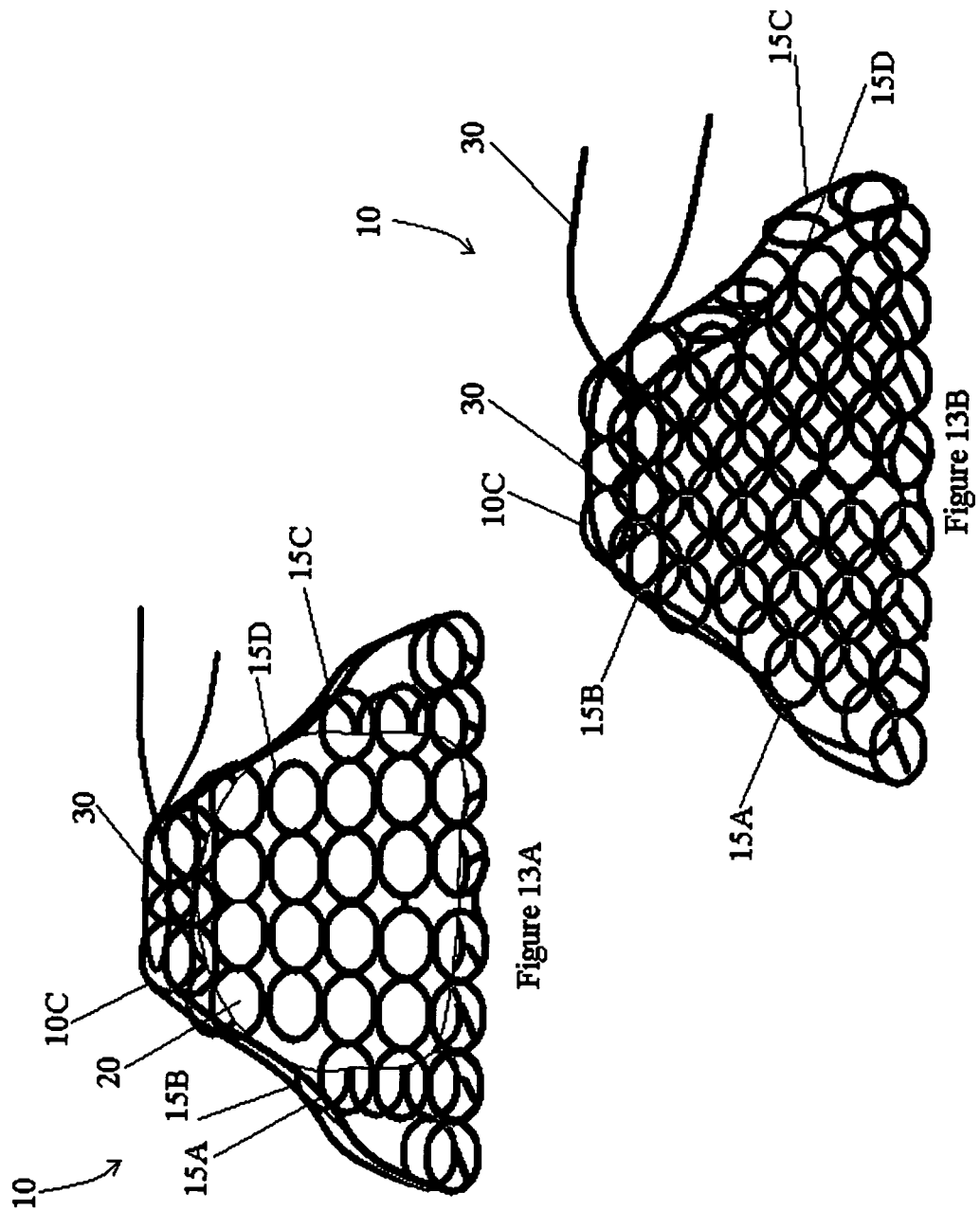

DEVICE AND METHOD FOR TRANSPORTING AND HANDLING TISSUE

RELATED APPLICATIONS

This application is a National Phase Application of PCT Patent Application No. PCT/IL2006/000288 having International Filing Date of Mar. 2, 2006, which claims the benefit of U.S. Provisional Patent Application No. 60/657,410 filed on Mar. 2, 2005. The contents of the above Applications are all incorporated herein by reference.

FIELD OF THE INVENTION

The present invention relates to a device and method for transporting and handling tissue.

BACKGROUND OF THE INVENTION

Tissue, being largely water or fat, does not maintain its shape. In consequence, positional reference of a tissue that has been removed, vis a vis its position and orientation in vivo, is nearly impossible. Yet at times, preserving the positional reference is highly desirable. For example, where a biopsy sample is taken, and only a portion of it is found cancerous, the positional reference is necessary, to determine where the cancerous tissue in the body may be. Similarly, where a lump of cancerous tissue is removed, without a margin of healthy tissue around it, i.e., without a "clean margin", thus indicating that some cancerous tissue may have been left in the body, the positional reference is necessary, to correlate the orientation of the removed tissue specimen with the body tissue.

Today, any one of two methods may be used for marking the orientation of the removed tissue. The first is known as the suture method. A surgeon marks a lateral edge of the removed tissue specimen with a long suture and a superior edge of the removed tissue specimen with a short suture. Yet, this method is inaccurate, as it is affected by changes in the removed tissue specimen during handling and transportation.

The second method is known as inking. The surgeon uses six colors of ink to mark the six faces of the removed tissue specimen. This method is rather demanding and involves much handling of the removed tissue specimen. Handling may be undesirable when the removed tissue specimen is yet to undergo pathological examinations.

U.S. Pat. No. 5,913,857, to Ritchart, et al., entitled, "Methods and devices for collection of soft tissue," provides a tissue sampling system for breast biopsies, intraoperative staging, laparoscopic surgery, lymphadenectomy and other procedures. Similarly, U.S. Pat. No. 6,007,497, to Huitema, entitled, "Surgical biopsy device," describes a biopsy probe for the collection of a soft tissue.

In these devices, the positional reference may be maintained through a rigid connection between a cutting tool and a carrying frame. However, where the tissue is first cut then transported to a carrying frame, the positional reference may be lost.

A device and method for transporting tissue while maintaining its positional reference, in a reliable manner, is desired.

SUMMARY OF THE INVENTION

The present invention overcomes the shortcomings of the presently known configurations by providing a device and method for tissue transport and handling, while maintaining the in-vivo tissue orientation. The device includes a structure, configured for receiving and holding a tissue specimen, wherein the tissue specimen includes tissue positional references; and device positional references, associated with the structure, for fixing the orientation of the tissue specimen, when held by the device, so as to reflect the tissue specimen positional references.

In accordance with one aspect of the present invention, there is thus provided a device for tissue handling, comprising:

a structure, configured for receiving and holding a tissue specimen, wherein the tissue specimen includes tissue positional references; and device positional references, associated with the structure, for fixing the orientation of the tissue specimen, when held by the device, so as to reflect the tissue specimen positional references.

Additionally, the device is configured to define tissue lateral and superior sides and a tissue top face.

Furthermore, the device is substantially transparent to at least one imaging modality, selected from the group consisting of x-ray imaging gamma imaging, and MRI.

Furthermore, the device is configured to receive the tissue specimen prior to its complete removal.

Additionally, the device positional references are built into the structure of the device.

Additionally, or alternatively, the device positional references are based on a color code.

Additionally, or alternatively, the device positional references are based on sutures of different lengths.

Additionally, the device is formed as a rigid body.

Alternatively, the device is formed as a flexible body.

Additionally, or alternatively, the device is formed as a stretchable body.

Additionally, or alternatively, the device is formed as an expansible body.

Alternatively, the device may be formed as a sac-like mesh.

Alternatively, the device may be formed as a stretchable stocking.

Alternatively, the device may be formed as a resilient cage.

Alternatively, the device may be formed as a box outline, comprising:

a box outline body;

a box outline lid; and at least one holder, for holding together the box outline body and lid.

Additionally, the structure comprises:

first and second frames, designed to be superimposed and receive and hold the tissue specimen therebetween; and at least one holder, for holding the first and second frames together, with the tissue specimen sandwiched therebetween, thus fixing the orientation of the tissue specimen.

Additionally, the at least one holder is a surgical latex band.

Additionally, the device may include a lining.

Furthermore, the device may include a grid.

Additionally, the device is configured for applying a force of less than 500 gram on the tissue specimen.

Furthermore, the device is configured for applying a force of between 20 and 200 gram on the tissue specimen.

Additionally, the device may further include at least one handle for holding the device.

Furthermore, the device may be provided in a plurality of sizes.

In accordance with one aspect of the present invention, there is thus provided a method for tissue transport and handling, comprising:

providing a device, which comprises:

a structure, configured for receiving and holding a tissue specimen, wherein the tissue specimen includes tissue positional references; and device positional references, associated with the structure, for fixing the orientation of the tissue specimen, when held by the device; and positioning the tissue specimen within the device, so as to reflect the tissue specimen positional references by the device positional references.

Additionally, the method includes maintaining the tissue specimen immobile, in the device.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A-1B schematically illustrate a device for tissue transport and handling, in accordance with some embodiments of the present invention;

FIGS. 2A-2B schematically illustrate a device for tissue transport and handling, when assembled, in accordance with some embodiments of the present invention;

FIGS. 3-4 schematically illustrate devices for tissue transport and handling, of different sizes, in accordance with some embodiments of the present invention;

FIGS. 5A-5D schematically illustrate a method of assembling a device for tissue transport and handling, in accordance with some embodiments of the present invention;

FIGS. 11A-11C schematically illustrate the device, formed as an outline of a box, in accordance with some embodiments of the present invention;

FIGS. 13A-13B schematically illustrate the device, formed as a sac-like mesh, in accordance with some embodiments of the present invention.

DESCRIPTION OF THE PREFERRED EMBODIMENTS

Figure 5C:
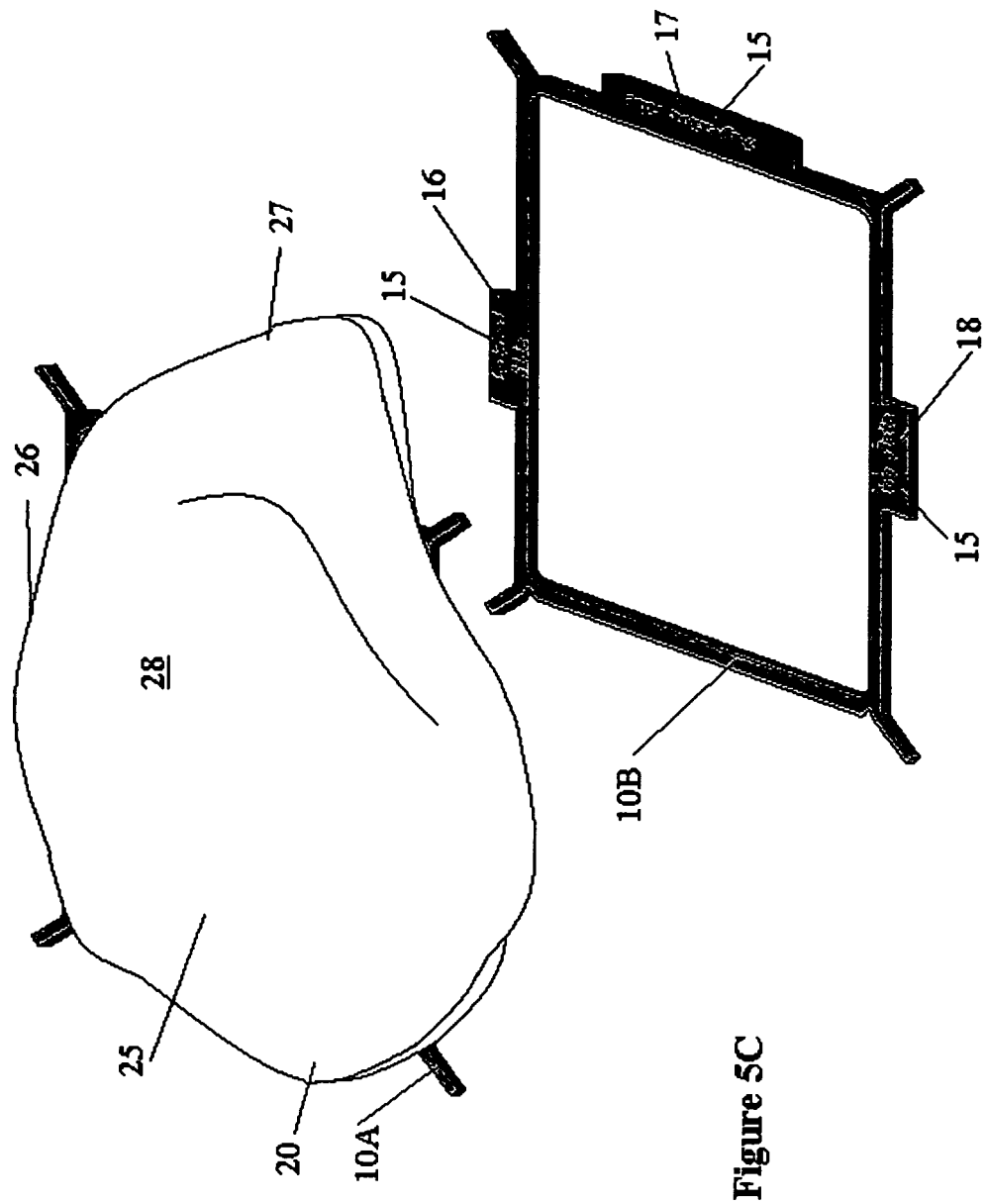

The present invention relates to a device and method for tissue transport and handling, while maintaining the in-vivo tissue orientation. The device includes a structure, configured for receiving and holding a tissue specimen, wherein the tissue specimen includes tissue positional references; and device positional references, associated with the structure, for fixing the orientation of the tissue specimen, when held by the device, so as to reflect the tissue specimen positional references.

The principles and operation of the device for tissue transport and handling, according to embodiments of the present invention, may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

Referring now to the drawings, FIGS. 1A-2B schematically illustrate a device 10 for tissue handling, in accordance with some embodiments of the present invention. FIGS. 1A and 1B illustrate the device 10 prior to deployment and FIGS. 2A and 2B illustrate the device 10 when holding a tissue specimen 20.

The device 10 includes a structure 10C, configured for receiving and holding a tissue specimen 20. The tissue specimen 20 has a specific positional reference with respect to the body from which it was taken, or is being taken, and the device 10 is designed to maintain the tissue positional reference, by providing a rigid frame of reference for it.

The device 10 may be used after the tissue specimen 20 has been removed from the body, or while the tissue specimen 20 is being removed.

In accordance with some embodiments, the tissue positional references may be marked on the tissue, for example, as a long suture 16A on a tissue lateral side, and as a short suture 17A on a tissue superior side. Alternatively, the tissue positional references are known but not marked.

Additionally, the structure 10C includes device positional references 15, for example, as a built-in design 15, for fixing the orientation of the tissue specimen 20, when held by the device 10, so as to reflect the positional references of the tissue specimen 20.

For example, the structure 10C may be formed of first and second frames 10A and 10B, designed to be superimposed and receive and hold the tissue specimen 20 therebetween. Additionally, the structure 10C may include holders 30, for holding the first and second frames 10A and 10B together, with the tissue specimen 20 sandwiched therebetween, thus fixing the orientation of the tissue specimen 20.

The positional references 15 may define a device lateral side 16, a device superior side 17, and a device top face 18. Alternatively, the positional references 15 may provide information from which the device lateral side 16, superior side 17, and top face 18 may be inferred, for example, by marking corners rather than sides.

As seen in FIG. 2A showing a superior view of the assembled device 10, the device 10 includes holders 30, for holding the first and second frames 10A and 10B together, when superimposed. A removed tissue specimen 20 is sandwiched therebetween.

As seen in FIG. 2B, showing a top view of the assembled device 10, the removed tissue specimen 20 is arranged within the device 10 so that a tissue lateral side 26, a tissue superior side 27, and a tissue top face 28 match the device lateral side 16, the device superior side 17, and the device top face 18, as indicated by the design 15.

The design 15 may include suture holes 19, for tying a long suture 16C on the device lateral side 16 and a short suture 17C on the device superior side 17. In FIGS. 2A and 2B, these are seen together with the long suture 16A on the tissue lateral side and the short suture 17A on the tissue superior side. It will be appreciated that the tissue statures 16A and 17A need not be used.

Alternatively, the design 15 may be any one of a mark, writing, a color code, a protrusion, or a notch, on the lateral side 16, the superior side 17, and the top face 18 of the device 10. Additionally or alternatively, any other manner of unequivocally defining the lateral side 16, the superior side 17, and the top face 18 of the device 10 may be employed.

Preferably, a cross-sectional area of the frames 10A and 10B is somewhat smaller than a cross sectional area of a face 25 of the removed tissue specimen 20. Thus, the removed tissue specimen 20 rests on the structure of the frames 10A and 10B.

Preferably, the frames 10A and 10B are rectangular in shape, having a width W, which is about 75% of a length L. For example, the length L may be about 60 mm and the width W may be about 45 mm. A frame width d, may be for example, about 2 mm. A frame thickness t, shown in FIGS. 5A and 5B, hereinbelow, may be, for example, between about 0.5 mm and about 1 mm. It will be appreciated that other dimensions and other proportions are similarly possible. For example, the length L may be between about 10 mm and about 100 mm and the width W may be, between about 7.5 mm and about 75 mm. Alternatively, other dimensions and other proportions, which may be larger or smaller, may be used. It will be appreciated that other shapes, for example, ellipses, may similarly be possible.

Preferably, the structure 10C is substantially transparent to x-ray and (or) gamma imaging. Additionally or alternatively, the structure 10C is substantially transparent to MRI. Thus, x-ray imaging, gamma imaging, and (or) MRI may be performed on the removed tissue specimen 20, when within the device 10.

Preferably, the frames 10A and 10B are rigid, to support the removed tissue specimen 20, but somewhat resilient.

Preferably, the frames 10A and 10B include handles 22, for example, corner handles, for holding the tissue sample, when arranged within the frames. The corner handles may extend out a distance h of about 10-15% the length of the length L, arranged for example, at an angle δ, for example, 60 degrees. It will be appreciated that other handles, of other shapes, may also be used.

The holders 30 may be surgical latex bands. Alternatively, ordinary rubber bands, ties, strings, clamps or other means of fastening the frames 10A and 10B together may be used. Notches 24 may be provided to keep the holders 30 in place.

An important consideration in the selection of the holders 30 is that they will be suitable for different widths of the removed tissue specimen 20, without exerting too much pressure on the removed tissue specimens 20. For example, when using surgical latex band, a force of between 20 and 200 gram may be generated on the removed tissue specimen 20. Preferably, the holders 30 will generate a force on the removed tissue specimen 20, which is no greater than 500 gm.

Referring further to the drawings, FIGS. 3 and 4 schematically illustrate a system of the devices 10 of varying sizes, in accordance with some embodiments of the present invention. For example, the device 10 of FIG. 3 has a length L1 and a width W1, and the device 10 of FIG. 4 has a length L2 and a width W2. Each of the devices 10 is used for a different size of the removed tissue specimen 20. Thus, a plurality of devices 10 may be provided, in increasing size increments of about 10% or 20%. It will be appreciated that other size increments may be employed.

Alternatively, expansible frames 10A and 10B may be provided, for example, with telescoping sides.

Referring further to the drawings, FIGS. 5A-5D schematically illustrate the method of utilizing the device 10, in accordance with some embodiments of the present invention.

As seen in FIGS. 5A and 5B, the frames 10A and 10B are provided with the design 15 for marking the lateral side 16, the superior side 17, and the top face 18 of the device 10.

As seen in FIG. 5C, the tissue specimen 20, having a cross section of the face 25, which is somewhat larger than the cross-section of the frames 10A and 10B, is placed on the first frame 10A. The placement is such that the tissue lateral side 26 is at the device lateral side 16, the tissue superior side 27 is at the device superior side 17, and the tissue top side 28 is facing up.

Figure 5D:
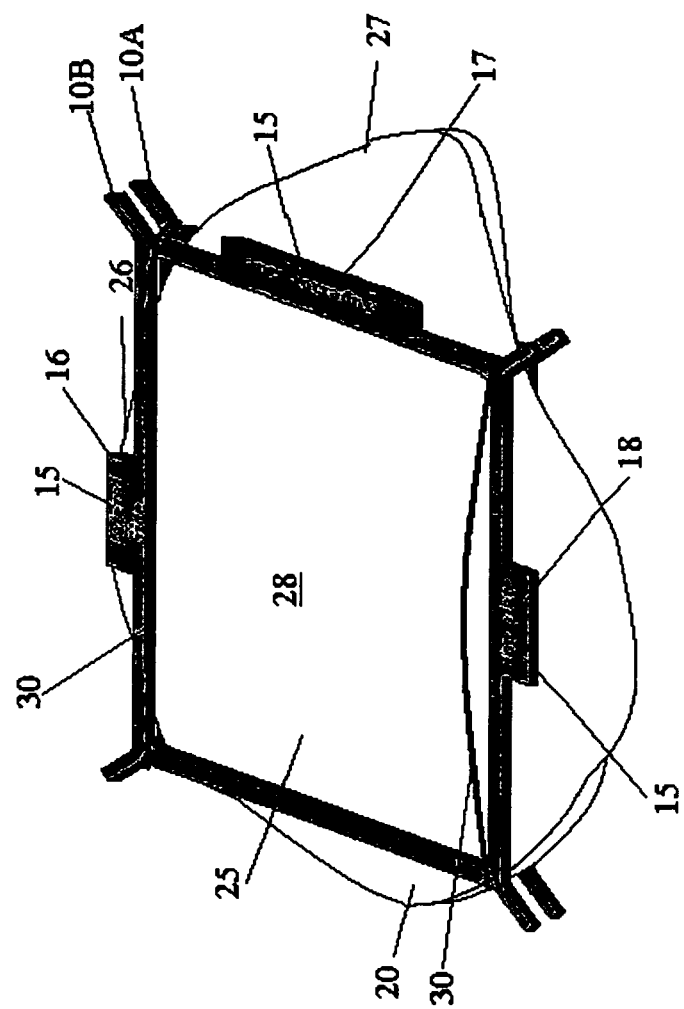

As seen in FIG. 5D, the second frame 10B is placed on the removed tissue specimen 20, and fastened with the holders 30.

Figure 6:
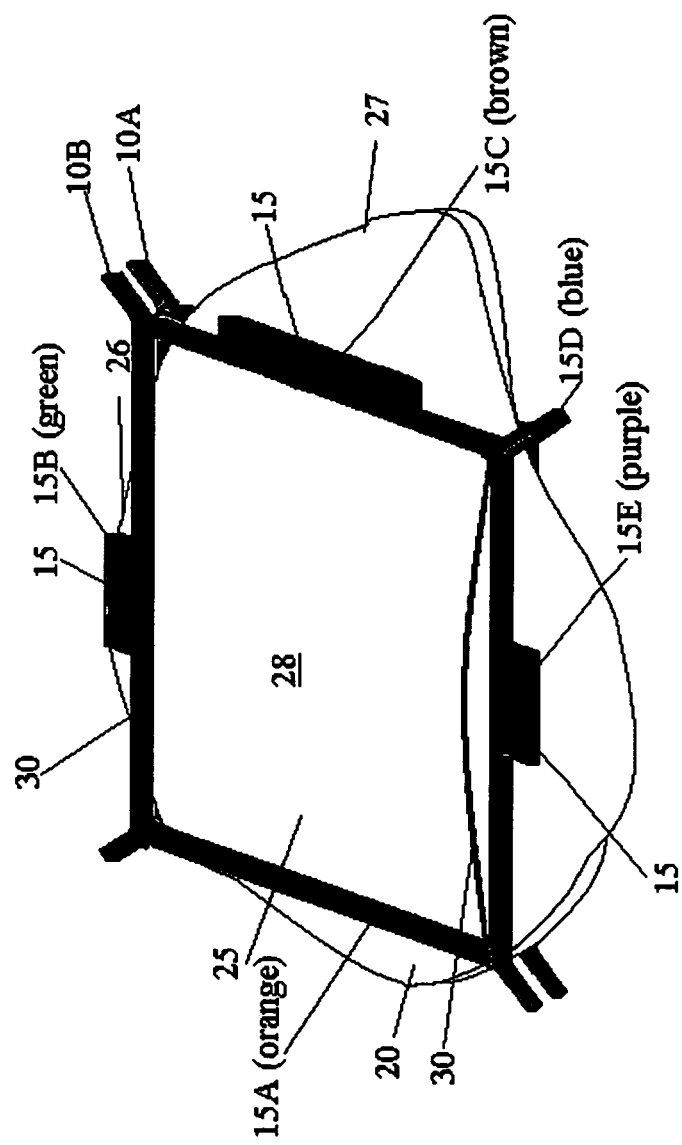
FIG. 6 schematically illustrates a color-coded device for tissue transport and handling, in accordance with some embodiments of the present invention.

Referring further to the drawings, FIG. 6 schematically illustrates the device 10, wherein the design 15 of the device positional references is a color code, in accordance with some embodiments of the present invention. For example, 15A may be orange, 15B may be green, representing the lateral side, 15C may be brown, representing the superior side, 15D may be blue, representing the bottom face, and 15E may be purple, representing the top face. A minimal color combination for defining the device's lateral and superior sides and the device's top face may be used. However, more colors may be used, where desired.

Figure 7:
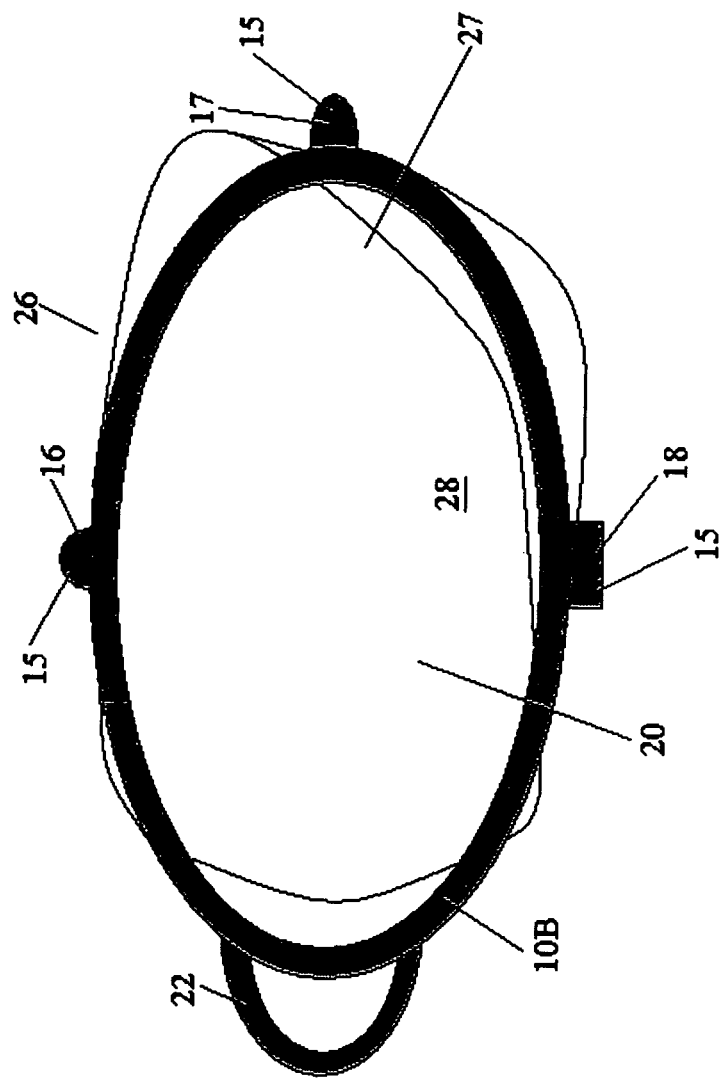
FIG. 7 schematically illustrates an elliptical device for tissue transport and handling, in accordance with some embodiments of the present invention.

Referring further to the drawings, FIG. 7 schematically illustrates the device 10, wherein the frames 10A and 10B and the handle 22 are elliptical, in accordance with some embodiments of the present invention. It will be appreciated that many other geometrical forms may be used, and are within the scope of the present invention.

Figure 8:
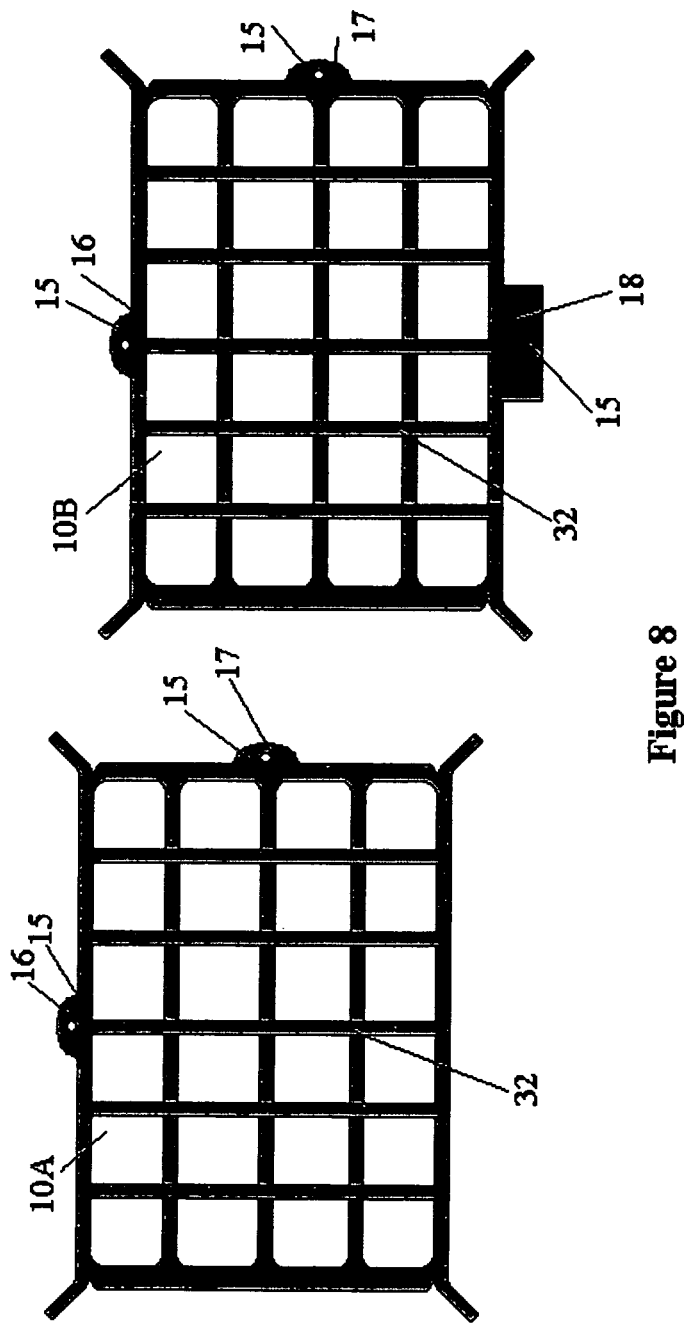
FIG. 8 schematically illustrates a device for tissue transport and handling, having an inner grid, in accordance with some embodiments of the present invention.

Referring further to the drawings, FIG. 8 schematically illustrates the device 10, having an inner grid 32, within the frames 10A and 10B, in accordance with some embodiments of the present invention. The grid 32 may be used for very small removed tissue specimens 20, for example, less than a cubic centimeter. The grid 32 may be substantially transparent to x-ray and gamma ray. Thus, the removed tissue specimens 20 may undergo these examinations while in the device 10. Additionally or alternatively, the grid 32 is substantially transparent to MRI.

Figure 9:
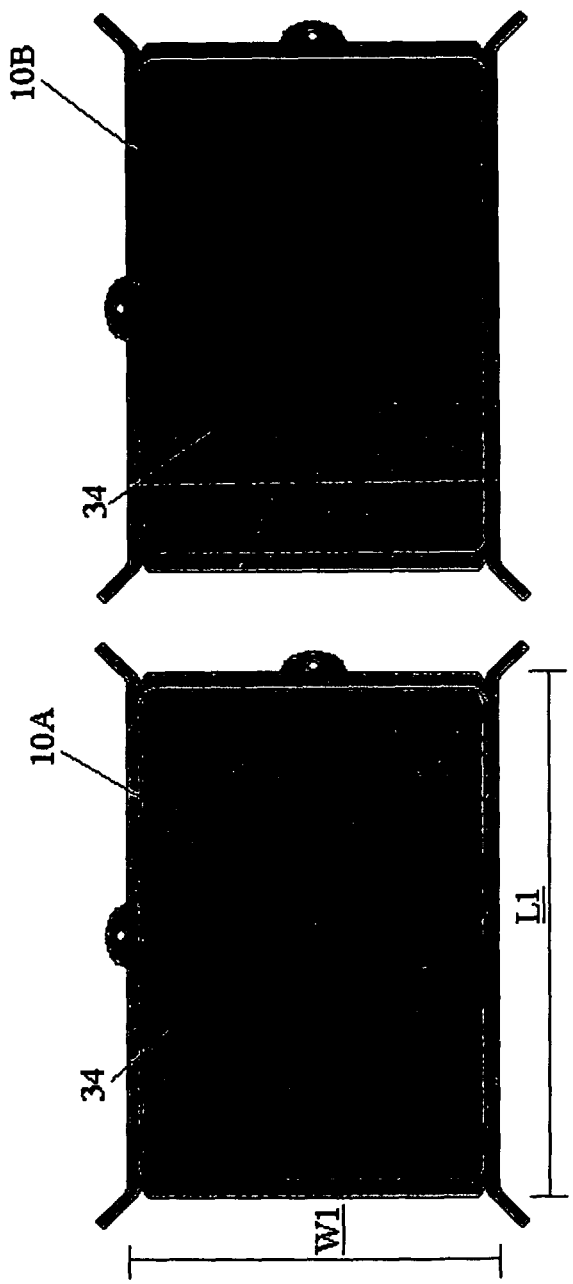
FIG. 9 schematically illustrates a device for tissue transport and handling, having a thin lining, in accordance with some embodiments of the present invention.

Referring further to the drawings, FIG. 9 schematically illustrates the device 10, having a thin lining 34, for example of plastic or nylon, in accordance with some embodiments of the present invention. The thin lining 34 may also be used for very small removed tissue specimens 20. Preferably, the thin lining is substantially transparent to x-ray and (or) gamma ray, so that the removed tissue specimens 20 may undergo these examinations while in the device 10. Additionally or alternatively, the thin lining is substantially transparent to MRI.

Figure 10:
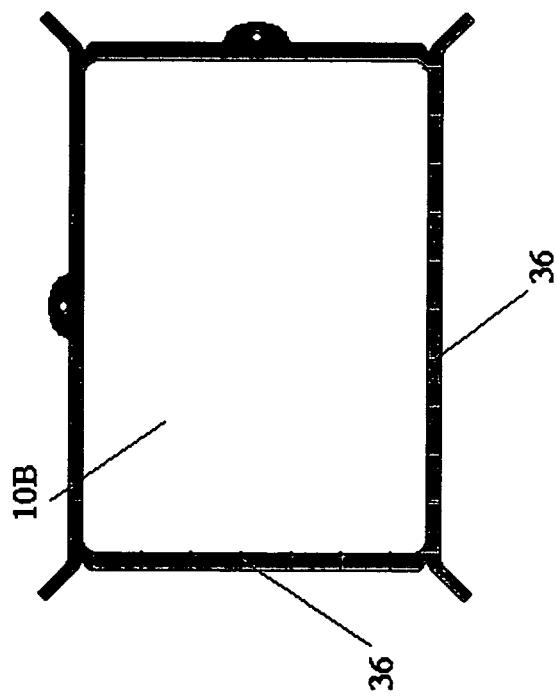
FIG. 10 schematically illustrates the device with graduations, in accordance with some embodiments of the present invention.

Referring further to the drawings, FIG. 10 schematically illustrates the device 10, used as a reference coordinate system, in accordance with some embodiments of the present invention. Any one of the frame 10A or 10B or both can be used as a reference coordinate system, for example, of x;y coordinates, for specifying locations on the removed tissue specimen 20. Both coarse and fine graduations may be employed.

Referring further to the drawings, FIGS. 11A-11C schematically illustrate the device 10, formed as an outline of a box, in accordance with some embodiments of the present invention. Accordingly, the structure 10C is formed of an outline of a box body 10A and an outline of a box lid 10B. A Color code may be employed. Additionally or alternatively, other positional references, such as 16 and 17 for defining the devices lateral and superior sides, may be used. The top face is inherently defined by the outline of the box lid 10B.

As seen in FIG. 11C, the tissue specimen 20 may be placed in the box body 10A and covered by the box lid 10B. The holders 30 may be used to keep the box body 10A and the box lid 10B together.

The present embodiment is useful for placing therein tissue specimen 20 even prior to complete removal. The tissue specimen 20 may be first placed in the outline of the box body 10A and then completely removed. After removal, the outline of the box lid 10B may be placed over the tissue specimen 20.

Figure 12C:
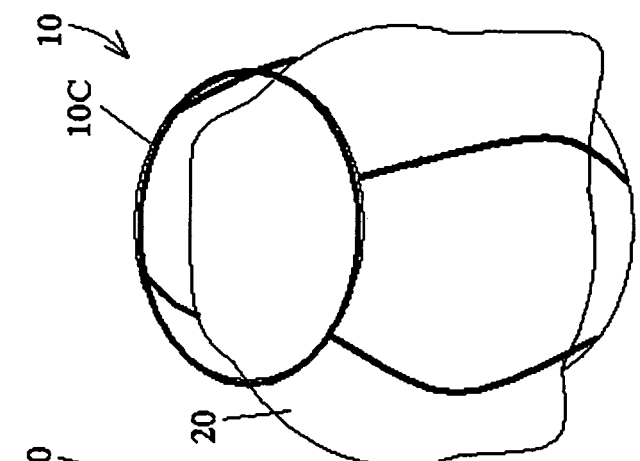
FIGS. 12A-12C schematically illustrate the device, formed as a resilient cage, in accordance with some embodiments of the present invention.
Figure 12B:
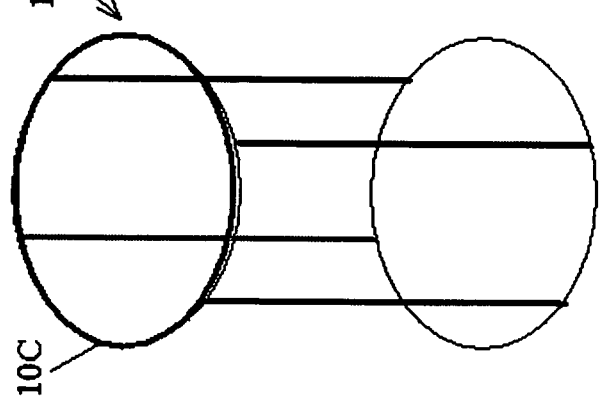
Figure 12A:
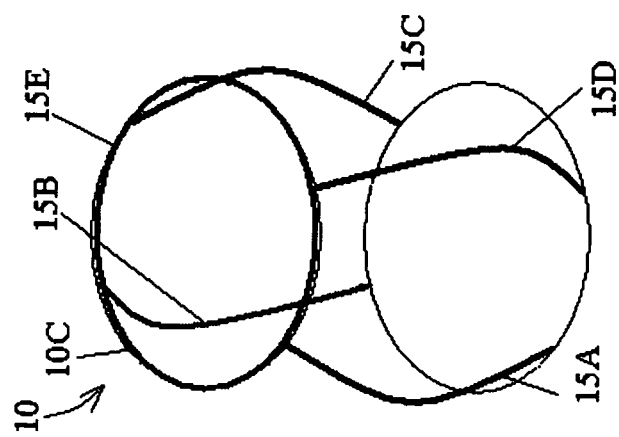

Referring further to the drawings, FIGS. 12A-12C schematically illustrate the device 10, formed as a color-coded resilient cage, in accordance with some embodiments of the present invention.

FIG. 12A illustrates the structure 10C, as a resilient cage, in its natural state.

FIG. 12B illustrates the structure 10C, as the resilient cage, when stretched and opened, to receive the tissue specimen 20.

FIG. 12C illustrates the structure 10C, as the resilient cage, holding the tissue specimen within.

The four colors 15A-15D define the lateral and superior orientations. At least one additional color, 15E, for example, purple, defines the top face.

Alternatively, positional references other than a color code may be employed.

The present embodiment may be placed on the tissue specimen 20 prior to its complete removal.

Referring further to the drawings, FIGS. 13A and 13B schematically illustrate the device 10, formed as a color-coded, sac-like mesh 10C, in accordance with some embodiments of the present invention.

The color-coded, sack-like mesh 10C includes a draw string 40, for forming a relatively tight fit over the tissue specimen 20. The draw string 40 is operative also to mark the top face. Additionally, the draw string 40 may form a loop, for carrying.

The present embodiment is different from the previous embodiments in being non-rigid. Therefore, the tissue specimen 20 may be examined from any direction, without being limited by the shape of the structure 10C, since it has no specific shape.

Additionally, the present embodiment may be placed on the tissue specimen 20 prior to its complete removal, and the draw string 40 may be drawn immediately with the removal.

Figure 14B:
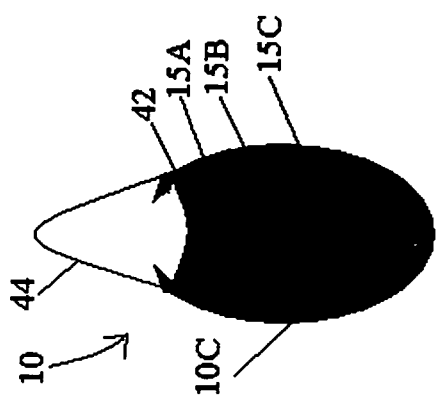
FIGS. 14A-14B schematically illustrate the device, formed as a resilient stocking-like device, in accordance with some embodiments of the present invention.
Figure 14A:
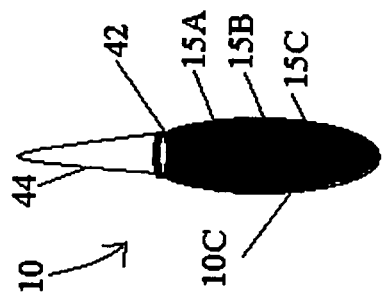

Referring further to the drawings, FIGS. 14A-14B schematically illustrate the device 10, formed as a color-coded, stretchable, stocking-like structure 10C, in accordance with some embodiments of the present invention.

The stretchable, stocking-like structure 10C may be stretched over the tissue specimen 20, to form a tight fit over it, while the color code maintains the tissue orientation. A stretchable orifice 42 allows the stocking-like structure 10C to receive the tissue specimen 20 and close over it, holding it within. A loop 44 may be used as a carrying handle.

Again, the present embodiment is non-rigid.

Additionally, the present embodiment may be placed on the tissue specimen 20 prior to its complete removal.

The advantages of the device 10, in accordance with the embodiments of the present invention, is that when placed within, the removed tissue specimen 20 may be handled, for example, carried, transported, maneuvered, rotated, examined by various techniques and otherwise manipulated, while its orientation remains fixed. In accordance with some embodiments, the device 10 is a rigid body. Alternatively, the device 10 maintains the orientation of the tissue even when not rigid, for example, as illustrated in FIGS. 13A and 13B.

Using the device 10, the six faces for the removed tissue specimen 20 may be defined and maintained, vis a vis the in-vivo orientation.

For example, the device 10 may allow easy handling of the removed tissue specimen 20 and clear approach to its faces 25 (FIG. 2B) without changing its initial orientation, Furthermore, the device 10 allows examination, such as x-ray imaging, gamma scanning, and (or) MRI when the tissue specimen 20 is within. Preferably, the structure 10C is essentially transparent to imaging by x-ray, gamma and (or) MR, so as not to interfere with the examination. For example, the structure 10C may be formed of a hydrocarbon polymer, so as to be transparent to x-ray and or gamma rays. Alternatively, the structure 10C may be formed of teflon or titanium, so as to be substantially transparent to MRI.

Additionally, different devices 10 may be provided for different tissue specimen sizes, so as to tailor fit to the required tissue specimen size. Additionally or alternatively, the device 10 may be stretchable or expansible.

It is expected that during the life of this patent many relevant devices for tissue transport and handling will be developed and the scope of the term device for tissue transport and handling is intended to include all such new technologies a priori.

As used herein the terms "about" and "substantially" refer to ±20%.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, any citation or identification of any reference in this application shall not be construed as an admission that such reference is available as prior art to the present invention.

What is claimed is:

1. A device for tissue handling, comprising:
   a structure, comprising soft tissue fixation devices, the soft tissue fixation parts being configured to receive and hold a removed soft tissue specimen, wherein the tissue specimen includes tissue positional references; and
   device positional references, associated with the structure, configured to fix the orientation of the soft tissue specimen to an in-vivo tissue orientation when held by the device, the in-vivo tissue orientation being an orientation of said tissue prior to removal, the orientation being so as to reflect the tissue specimen positional references and wherein the structure is a first outline frame designed to receive and hold the tissue specimen therebetween, the structure further having at least one holder, for holding the first outline frame with the tissue specimen, the structure forming six faces, in a manner allowing a clear approach to each of said six faces to enter for manipulation of said tissue specimen, and fixing the orientation of the tissue specimen, the approach to said specimen at each face for said entry for manipulation and fixing not being limited by said structure, wherein the device positional references are based on one member of the group consisting of a color code and on sutures of different lengths.

2. The device of claim 1, configured to define tissue lateral and superior sides and a tissue top face.

3. The device of claim 1, wherein the device is substantially transparent to at least one imaging modality, selected from the group consisting of x-ray imaging gamma imaging, and MRI.

4. The device of claim 1, configured to receive the tissue specimen prior to its complete removal.

5. The device of claim 1, wherein the device positional references are built into the structure of the device.

6. The device of claim 1, formed as a rigid body.

7. The device of claim 1, formed as an expansible body.

8. The device of claim 1, wherein the structure further comprises:
   a second frame, said first and second frames, designed to be superimposed and receive and hold the tissue specimen therebetween; and wherein said at least one holder is further configured for holding the first and second frames together, with the tissue specimen sandwiched therebetween, thus fixing the orientation of the tissue specimen.

9. The device of claim 1, provided in a plurality of sizes.

10. A device for tissue handling, comprising:
    a structure, comprising soft tissue fixation devices, the soft tissue fixation parts being configured to receive and hold a removed soft tissue specimen, wherein the tissue specimen includes tissue positional references; and
    device positional references, associated with the structure, configured to fix the orientation of the soft tissue specimen to an in-vivo tissue orientation when held by the device, the in-vivo tissue orientation being an orientation of said tissue prior to removal, the orientation being so as to reflect the tissue specimen positional references and wherein the structure is a first outline frame designed to receive and hold the tissue specimen therebetween, the structure further having at least one holder, for holding the first outline frame with the tissue specimen, the structure forming six faces, in a manner allowing a clear approach to each of said six faces to enter for manipulation of said tissue specimen, and fixing the orientation of the tissue specimen, the approach to said specimen at each face for said entry for manipulation and fixing not being limited by said structure, formed as one member of the group consisting of a flexible body and a stretchable body.

11. A device for tissue handling, comprising:
    a structure, comprising soft tissue fixation devices, the soft tissue fixation parts being configured to receive and hold a removed soft tissue specimen, wherein the tissue specimen includes tissue positional references; and
    device positional references, associated with the structure, configured to fix the orientation of the soft tissue specimen to an in-vivo tissue orientation when held by the device, the in-vivo tissue orientation being an orientation of said tissue prior to removal, the orientation being so as to reflect the tissue specimen positional references and wherein the structure is a first outline frame designed to receive and hold the tissue specimen therebetween, the structure further having at least one holder, for holding the first outline frame with the tissue specimen, the structure forming six faces, in a manner allowing a clear approach to each of said six faces to enter for manipulation of said tissue specimen, and fixing the orientation of the tissue specimen, the approach to said specimen at each face for said entry for manipulation and fixing not being limited by said structure, wherein the device is formed as a resilient cage.

12. A device for tissue handling, comprising:
    a structure, comprising soft tissue fixation devices, the soft tissue fixation parts being configured to receive and hold a removed soft tissue specimen, wherein the tissue specimen includes tissue positional references; and
    device positional references, associated with the structure, configured to fix the orientation of the soft tissue specimen to an in-vivo tissue orientation when held by the device, the in-vivo tissue orientation being an orientation of said tissue prior to removal, the orientation being so as to reflect the tissue specimen positional references and wherein the structure is a first outline frame designed to receive and hold the tissue specimen therebetween, the structure further having at least one holder, for holding the first outline frame with the tissue specimen, the structure forming six faces, in a manner allowing a clear approach to each of said six faces to enter for manipulation of said tissue specimen, and fixing the orientation of the tissue specimen, the approach to said specimen at each face for said entry for manipulation and fixing not being limited by said structure, wherein said first frame is formed as a box outline, comprising:
    a box outline body;
    a box outline lid; and
    at least one holder, for holding together the box outline body and lid.

13. The device of claim 12, and wherein the at least one holder is a surgical latex band.

14. The device of claim 12, and further including a grid.

15. A device for tissue handling, comprising:
    a structure, comprising soft tissue fixation devices, the soft tissue fixation parts being configured to receive and hold a removed soft tissue specimen, wherein the tissue specimen includes tissue positional references; and
    device positional references, associated with the structure, configured to fix the orientation of the soft tissue specimen to an in-vivo tissue orientation when held by the device, the in-vivo tissue orientation being an orientation of said tissue prior to removal, the orientation being so as to reflect the tissue specimen positional references and wherein the structure is a first outline frame designed to receive and hold the tissue specimen therebetween, the structure further having at least one holder, for holding the first outline frame with the tissue specimen, the structure forming six faces, in a manner allowing a clear approach to each of said six faces to enter for manipulation of said tissue specimen, and fixing the orientation of the tissue specimen, the approach to said specimen at each face for said entry for manipulation and fixing not being limited by said structure, configured for applying a force comprising one member of the group consisting of less than 500 gram on the tissue specimen and between 20 and 200 gram on the tissue specimen.

16. A device for tissue handling, comprising:
a structure, comprising soft tissue fixation devices, the soft tissue fixation parts being configured to receive and hold a removed soft tissue specimen, wherein the tissue specimen includes tissue positional references; and
device positional references, associated with the structure, configured to fix the orientation of the soft tissue specimen to an in-vivo tissue orientation when held by the device, the in-vivo tissue orientation being an orientation of said tissue prior to removal, the orientation being so as to reflect the tissue specimen positional references and wherein the structure is a first outline frame designed to receive and hold the tissue specimen therebetween, the structure further having at least one holder, for holding the first outline frame with the tissue specimen, the structure forming six faces, in a manner allowing a clear approach to each of said six faces to enter for manipulation of said tissue specimen, and fixing the orientation of the tissue specimen, the approach to said specimen at each face for said entry for manipulation and fixing not being limited by said structure, and further including handles for holding the device.

17. A method for tissue transport and handling, comprising:
providing a device, which comprises:
a structure, having at least one soft tissue holding part to receive and hold a removed soft tissue specimen, wherein the soft tissue specimen includes tissue positional references, wherein the structure is a first outline frame, designed to receive and hold the tissue specimen in an in vivo orientation, said in vivo orientation being an orientation of said tissue prior to removal, the structure further having:
at least one holder, for holding the first outline frame with the tissue specimen, said holding providing said structure with six faces, and fixing the orientation of the tissue specimen in a manner allowing a clear approach to each of said six faces to enter for manipulation of said specimen, the approach to said specimen at each face for said entry for manipulation and fixing not being limited by said structure; and
device positional references, associated with the structure, for fixing the orientation of the tissue specimen, when held by the device;
the method further comprising
positioning the tissue specimen within the device, so as to reflect the tissue specimen positional references by the device positional references, wherein the device positional references are based on one member of the group consisting of a color code and on sutures of different lengths.

18. The method of claim 17, and further including maintaining the tissue specimen immobile, in the device.

19. The method of claim 17, wherein the device is configured to define tissue lateral and superior sides and a tissue top face.

20. The method of claim 17, wherein the device is substantially transparent to at least one imaging modality, selected from the group consisting of x-ray imaging gamma imaging, and MRI.

21. The method of claim 17, wherein the device is configured to receive the tissue specimen prior to its complete removal.

22. The method of claim 17, wherein the device positional references are built into the structure of the method.

23. The method of claim 17, wherein the device is formed as a rigid body.

24. The method of claim 17, wherein the device is formed as an expansible body.

25. A method for tissue transport and handling, comprising:
providing a device, which comprises:
a structure, having at least one soft tissue holding part to receive and hold a removed soft tissue specimen, wherein the soft tissue specimen includes tissue positional references, wherein the structure is a first outline frame, designed to receive and hold the tissue specimen in an in vivo orientation, said in vivo orientation being an orientation of said tissue prior to removal, the structure further having:
at least one holder, for holding the first outline frame with the tissue specimen, said holding providing said structure with six faces, and fixing the orientation of the tissue specimen in a manner allowing a clear approach to each of said six faces to enter for manipulation of said specimen, the approach to said specimen at each face for said entry for manipulation and fixing not being limited by said structure; and
device positional references, associated with the structure, for fixing the orientation of the tissue specimen, when held by the device;
the method further comprising
positioning the tissue specimen within the device, so as to reflect the tissue specimen positional references by the device positional references, wherein the device is formed as one member of the group consisting of a flexible body and a stretchable body.

26. A method for tissue transport and handling, comprising:
providing a device, which comprises:
a structure, having at least one soft tissue holding part to receive and hold a removed soft tissue specimen, wherein the soft tissue specimen includes tissue positional references, wherein the structure is a first outline frame, designed to receive and hold the tissue specimen in an in vivo orientation, said in vivo orientation being an orientation of said tissue prior to removal, the structure further having:
at least one holder, for holding the first outline frame with the tissue specimen, said holding providing said structure with six faces, and fixing the orientation of the tissue specimen in a manner allowing a clear approach to each of said six faces to enter for manipulation of said specimen, the approach to said specimen at each face for said entry for manipulation and fixing not being limited by said structure; and device positional references, associated with the structure, for fixing the orientation of the tissue specimen, when held by the device;

the method further comprising positioning the tissue specimen within the device, so as to reflect the tissue specimen positional references by the device positional references, wherein the device is formed as a resilient cage.

27. A method for tissue transport and handling, comprising:

providing a device, which comprises:

a structure, having at least one soft tissue holding part to receive and hold a removed soft tissue specimen, wherein the soft tissue specimen includes tissue positional references, wherein the structure is a first outline frame, designed to receive and hold the tissue specimen in an in vivo orientation, said in vivo orientation being an orientation of said tissue prior to removal, the structure further having:

at least one holder, for holding the first outline frame with the tissue specimen, said holding providing said structure with six faces, and fixing the orientation of the tissue specimen in a manner allowing a clear approach to each of said six faces to enter for manipulation of said specimen, the approach to said specimen at each face for said entry for manipulation and fixing not being limited by said structure; and device positional references, associated with the structure, for fixing the orientation of the tissue specimen, when held by the device;

the method further comprising positioning the tissue specimen within the device, so as to reflect the tissue specimen positional references by the device positional references, wherein said first frame is formed as box outline, the outline comprising:

a box outline body;

a box outline lid; and at least one holder, for holding together the box outline body and lid.

28. The method of claim 27, and wherein the at least one holder is a surgical latex band.

29. The method of claim 27, wherein the device further includes a lining.

30. The method of claim 27, wherein the device further includes a grid.

31. A method for tissue transport and handling, comprising:

providing a device, which comprises:

a structure, having at least one soft tissue holding part to receive and hold a removed soft tissue specimen, wherein the soft tissue specimen includes tissue positional references, wherein the structure is a first outline frame, designed to receive and hold the tissue specimen in an in vivo orientation, said in vivo orientation being an orientation of said tissue prior to removal, the structure further having:

at least one holder, for holding the first outline frame with the tissue specimen, said holding providing said structure with six faces, and fixing the orientation of the tissue specimen in a manner allowing a clear approach to each of said six faces to enter for manipulation of said specimen, the approach to said specimen at each face for said entry for manipulation and fixing not being limited by said structure; and device positional references, associated with the structure, for fixing the orientation of the tissue specimen, when held by the device;

the method further comprising positioning the tissue specimen within the device, so as to reflect the tissue specimen positional references by the device positional references, wherein the structure comprises a second frame, the first and second frames, designed to be superimposed and receive and hold the tissue specimen therebetween; and wherein said at least one holder is further configured for holding the first and second frames together, with the tissue specimen sandwiched therebetween, thus fixing the orientation of the tissue specimen.

32. The method of claim 31, and wherein the at least one holder is a surgical latex band.

33. The method of claim 31, wherein the device further includes a grid.

34. A method for tissue transport and handling, comprising:

providing a device, which comprises:

a structure, having at least one soft tissue holding part to receive and hold a removed soft tissue specimen, wherein the soft tissue specimen includes tissue positional references, wherein the structure is a first outline frame, designed to receive and hold the tissue specimen in an in vivo orientation, said in vivo orientation being an orientation of said tissue prior to removal, the structure further having:

at least one holder, for holding the first outline frame with the tissue specimen, said holding providing said structure with six faces, and fixing the orientation of the tissue specimen in a manner allowing a clear approach to each of said six faces to enter for manipulation of said specimen, the approach to said specimen at each face for said entry for manipulation and fixing not being limited by said structure; and device positional references, associated with the structure, for fixing the orientation of the tissue specimen, when held by the device;

the method further comprising positioning the tissue specimen within the device, so as to reflect the tissue specimen positional references by the device positional references, and further including applying a force on the tissue specimen, said force being one member of the group consisiting of less than 500 gram, and between 20 and 200 gram.

35. A device for tissue handling, comprising:

a structure, comprising soft tissue fixation devices, the soft tissue fixation parts being configured to receive and hold a removed soft tissue specimen, wherein the tissue specimen includes tissue positional references; and device positional references, associated with the structure, configured to fix the orientation of the soft tissue specimen to an in-vivo tissue orientation when held by the device, the in-vivo tissue orientation being an orientation of said tissue prior to removal, the orientation being so as to reflect the tissue specimen positional references and wherein the structure is a first outline frame designed to receive and hold the tissue specimen therebetween, the structure further having at least one holder, for holding the first outline frame with the tissue specimen, the structure forming six faces, in a manner allowing a clear approach to each of said six faces to enter for manipulation of said tissue specimen, and fixing the orientation of the tissue specimen, the approach to said specimen at each face for said entry for manipulation and fixing not being limited by said structure, wherein the structure further comprises:

a second frame, said first and second frames, designed to be superimposed and receive and hold the tissue specimen therebetween; and wherein said at least one holder is further configured for holding the first and second frames together, with the tissue specimen sandwiched therebetween, thus fixing the orientation of the tissue specimen, and wherein the at least one holder is a surgical latex band.

36. A device for tissue handling, comprising:

a structure, comprising soft tissue fixation devices, the soft tissue fixation parts being configured to receive and hold a removed soft tissue specimen, wherein the tissue specimen includes tissue positional references; and device positional references, associated with the structure, configured to fix the orientation of the soft tissue specimen to an in-vivo tissue orientation when held by the device, the in-vivo tissue orientation being an orientation of said tissue prior to removal, the orientation being so as to reflect the tissue specimen positional references and wherein the structure is a first outline frame designed to receive and hold the tissue specimen therebetween, the structure further having at least one holder, for holding the first outline frame with the tissue specimen, the structure forming six faces, in a manner allowing a clear approach to each of said six faces to enter for manipulation of said tissue specimen, and fixing the orientation of the tissue specimen, the approach to said specimen at each face for said entry for manipulation and fixing not being limited by said structure, wherein the structure further comprises:

a second frame, said first and second frames, designed to be superimposed and receive and hold the tissue specimen therebetween; and wherein said at least one holder is further configured for holding the first and second frames together, with the tissue specimen sandwiched therebetween, thus fixing the orientation of the tissue specimen, and further including one member of the group comprising a lining and a grid.

* * * * *